United States Patent
Schmidt et al.

(10) Patent No.: US 12,174,138 B2
(45) Date of Patent: Dec. 24, 2024

(54) WET GAS CAPACITANCE PROBE

(71) Applicant: Spartek Systems, Inc., Sylvan Lake (CA)

(72) Inventors: Mathew G. Schmidt, Houston, TX (US); Troy M. Thiele, Sylvan Lake (CA)

(73) Assignee: SPARTEK SYSTEMS, INC., Sylvan Lake (CA)

( * ) Notice: Subject to any disclaimer, the term of this patent is extended or adjusted under 35 U.S.C. 154(b) by 196 days.

(21) Appl. No.: 17/957,855

(22) Filed: Sep. 30, 2022

(65) Prior Publication Data

US 2023/0029571 A1    Feb. 2, 2023

Related U.S. Application Data

(63) Continuation-in-part of application No. 16/664,359, filed on Oct. 25, 2019, now Pat. No. 11,486,847.

(51) Int. Cl.
G01N 27/22    (2006.01)
G01N 33/28    (2006.01)

(52) U.S. Cl.
CPC ......... G01N 27/226 (2013.01); G01N 27/221 (2013.01); G01N 33/2847 (2013.01)

(58) Field of Classification Search
CPC ............ G01N 27/221; G01N 33/2823; G01N 33/2852; G01N 33/2847; G01N 33/5438
See application file for complete search history.

(56) References Cited

U.S. PATENT DOCUMENTS

| | | | |
|---|---|---|---|
| 2,907,945 A | 10/1959 | Bucci | |
| 5,478,267 A * | 12/1995 | McDonald | A63H 33/28 446/485 |
| 5,562,610 A * | 10/1996 | Brumbach | A61B 17/320068 601/3 |
| 10,177,696 B1 | 1/2019 | Holladay et al. | |
| 2012/0215449 A1 | 8/2012 | Hallundb | |
| 2013/0110411 A1 | 5/2013 | Black | |
| 2014/0043044 A1 | 2/2014 | Parker | |
| 2014/0102181 A1 | 4/2014 | Mohajer | |
| 2015/0293254 A1* | 10/2015 | Wang | E21B 49/00 324/355 |
| 2019/0118153 A1* | 4/2019 | Yang | A23J 3/04 |
| 2019/0189880 A1 | 6/2019 | Lin | |
| 2019/0387604 A1* | 12/2019 | Fandrich | H05H 1/2406 |
| 2020/0072594 A1* | 3/2020 | Potter | H01J 37/32807 |
| 2020/0102232 A1 | 4/2020 | Holland | |
| 2020/0365315 A1* | 11/2020 | Kim | H01F 41/046 |
| 2020/0393398 A1* | 12/2020 | Smith | G01N 27/06 |

* cited by examiner

*Primary Examiner* — Christopher P McAndrew
*Assistant Examiner* — Zannatul Ferdous
(74) *Attorney, Agent, or Firm* — D'Ambrosio & Menon, PLLC; Usha Menon

(57) ABSTRACT

A capacitance probe for determining the water cut or the amount of water in fluids. The probe includes at least a pair of electrodes. Each electrode includes a thin, pliable and conductive winding. The windings have a thin insulation layer or coating. The first electrode and the second electrode are configured to form a capacitance sensor that generates a signal related to the dielectric permittivity of a fluid flowing between the first electrode and the second electrode.

10 Claims, 4 Drawing Sheets

WET GAS CAPACITANCE PROBE

CROSS-REFERENCE TO RELATED APPLICATIONS

This application is a continuation-in-part of and claims priority to U.S. application Ser. No. 16/664,359, entitled "Method and Apparatus for Determining Water Content of a Fluid", filed on Oct. 25, 2019, the contents of which are incorporated herein by reference in its entirety.

FIELD OF THE INVENTION

The present invention relates to probes for measuring the water content in fluids produced downhole in an oil or gas well.

BACKGROUND

A capacitor is a device that consists of two conductive plates or electrode plates that are separated by an insulator or a dielectric medium/material. Capacitance is an electrical property of capacitors. It is a measure of the amount of charge that a capacitor can hold at a given voltage. Capacitance (C) is measured in Farad (F) and it can be defined by the unit coulomb per volt:

$$C = \frac{Q}{V} \quad \text{Equation 1}$$

where,
C is the capacitance in farad (F),
Q is the magnitude of the charge stored on each plate (coulomb), and
V is the applied voltage to the plates (volts).

When a voltage is applied across the two electrodes of the capacitor, the conducting plates will start to store electrical energy until the potential difference across the capacitor matches with the source voltage. The time required to fully charge a capacitor is determined by the Time Constant ($\tau$). The value of the time constant describes the time it takes to charge a capacitor to 63% of its total capacity. The time constant ($\tau$) is measured in seconds and can be defined as:

$$\tau = R\,C \quad \text{Equation 2}$$

where,
R is the resistance of the resistor connected in line with the capacitor,
C is the capacitance of the capacitor.

The capacitance of a capacitor depends on the geometry of the electrodes and not on the external source of charge or potential difference. In general, the capacitance is determined by the dielectric material, distance between electrode plates, and the area of each electrode. For capacitors with two parallel electrode plates, the capacitance can be expressed in terms of its geometry and dielectric constant as:

$$C = \varepsilon_r \frac{\varepsilon_0 A}{d} \quad \text{Equation 3}$$

where,
C is the capacitance in farad (F),
$\varepsilon$ is the permittivity of the dielectric material, $\varepsilon_r \times \varepsilon_0$
$\varepsilon_r$ is the relative static permittivity (or dielectric constant) of the material between the plates,
$\varepsilon_0$ is the permittivity of free space, which is equal to $8.854 \times 10^{-12}$ F/m;
A is the area of each plate, in square meters and
d is the separation distance (in meters) of the two plates.

In the case of a capacitance sensor for a logging tool, the geometry is a little more complex, but the same basic principles apply, namely:
a) An increase in area of the electrode (length and/or diameter) will increase the capacitance;
b) A decrease in the spacing between the electrodes will increase the capacitance; or
c) An increase in the dielectric constant of the fluid will increase the capacitance will increase.

The capacitance measurement of logging tools relies on the change in the permittivity or dielectric constant of the fluid to differentiate between water and hydrocarbons.

Table 1 shows the relative permittivity/dielectric constant/dielectric permittivity for some common materials.

TABLE 1

| Material | Dielectric Constant |
| --- | --- |
| Air (dry) | 1.000536 |
| Ceramic | 21-38 |
| Petroleum | 2.0-2.2 |
| PEEK (polyetheretherketone) | 3.2 |
| Teflon | 2.1 |
| Water | 80.0 |

The capacitance probe, once it is lowered into a wellbore, can measure the dielectric permittivity of the fluid (water, oil, and/or gas) passing through it. Water has a high dielectric constant which can be distinguished from oil or gas. As water typically coexists with crude oil in petroleum reservoirs, water content, or water cut is an important measure for monitoring wellbore production operations. Water cut measurements are used during production operations in feasibility analyses of oil wells, to determine rates for introducing fluids into a formation or well during recovery methods, in monitoring refining processes, for managing pipeline use, and other such processes.

FIG. 1 represents an exemplary conventional capacitance probe or sensor 100 in a production logging tool. The capacitance probe 100 is generally composed of two electrodes—an insulated primary electrode 110 and a secondary electrode 120. The insulated primary electrode 110 includes a primary electrode 112—comprising a plate or a cylinder—and insulation material 114 for the primary electrode. The secondary electrode 120 is usually the body of the tool. The insulated primary electrode 110 and the secondary electrode 120 are separated from each other by a dielectric medium (such as, a wellbore fluid) 130. The fluid 125 flows between the insulated primary electrode 110 and the tool body 120.

The capacitance measurement of production logging tools relies on the change in the permittivity or dielectric constant of the fluid to differentiate between water and hydrocarbons.

Wetting occurs when a film of conductive fluid adheres to the surface of the electrodes which may cause inaccurate measurements of capacitance. For instance, the capacitance probe may sense a higher capacitance than what would be expected based on the fluids surrounding the probe. One source of the wetting is water fallback which causes water to drip on to the capacitance probe creating erroneous readings. Wetting is especially problematic in a wet gas well. In these wells, only a small percentage of the produced fluids is water, sometimes less than 10%, but due to wetting, a false reading of 40% or higher may be observed on the conventional capacitance probes. Other sources of wetting include condensation of water vapor, and multiphase flow. In these cases, water has "wetted" the probe providing erroneous readings as described in this paragraph.

As described in FIG. 1, conventional production logging tools utilize an insulated primary electrode in the center of the tool body and uses the metal of the tool body as the second electrode. Wetting of this "center lined" primary electrode can cause problematic/erroneous readings. Similarly, the dynamic range of the probe, that is, the range of acceptable measurement, is also limited by the outer surface area of the electrodes, the thickness of the insulating material, and the dielectric properties of the insulating material.

Therefore, there is a need for novel capacitance probes for measuring water cut, optimizing sampled fluids and minimizing the impact of spurious responses by reducing their magnitudes.

SUMMARY

The present invention is an improved wet gas capacitance probe (or "probe") for determining the water cut in fluids produced downhole in an oil or gas well. The probe is configured to determine the water cut of fluids (such as, water, oil and/or gas) that are produced downhole by measuring the dielectric constant of the fluid while reducing the impact due to wetting. The probe has an increased dynamic range between water, oil and gas. This improvement increases both the accuracy and sensitivity of the measurement to small changes in water cut. The probe can be incorporated into a logging sonde that is lowered into the well. The probe can be sampled multiple times a second by a downhole electronic circuit. The data from these measurements can be either transmitted to the surface of the well by a wireline telemetry system or it can be stored downhole for later retrieval and processing.

According to an embodiment, a wet gas capacitance probe of the invention includes at least one pair of electrodes, wherein the electrodes comprise insulated conductive wires or windings. However, it is understood the one or more embodiments of the invention encompass any conductive article that is insulated and can mimic the function of the conductive windings. Additionally, the invention can also be implemented with rigid wires or other conductive shapes/articles.

The windings can be configured to form a capacitance sensor that can generate a signal related to the dielectric permittivity of the fluid. In one or more embodiments, the windings can include a thin insulation layer or coating. The windings can be oriented differently, such as, in different planes, to optimize measurement of the produced fluids. The capacitance is measured between the two insulated windings or electrodes.

In one embodiment, one of the insulated windings/electrodes is configured as a guard electrode. In another embodiment, additional electrodes can be used to act as guard electrodes or to make the measurements at different cross-sectional areas.

According to an embodiment, a capacitance probe for determining in-situ water content of a conductive fluid, comprises: at least two electrodes, each electrode comprising: a thin, pliable and conductive wire or winding; and a thin layer or coating of an insulating material, wherein the insulating material covers the conductive wire. The insulating material is a thermosetting polymer. A first electrode is configured as a primary electrode, and a second electrode is configured as a secondary electrode. The primary electrode and the secondary electrode are separated from each other by a predetermined distance. The primary electrode is arranged parallel to the secondary electrode such that the capacitance probe has a substantially large effective surface area that is sensitive to the conductive fluid. The secondary electrode can be electrically isolated from the conductive fluid. The primary electrode and the secondary electrode are configured to form a capacitance sensor that generates a signal related to the dielectric permittivity of the conductive fluid, wherein the conductive fluid flows over and between the primary and secondary electrodes. The capacitance probe can be located within a body of a logging tool. The capacitance probe can include a sleeve for the electrodes. The conductive fluid comprises a multiphase mixture of water, oil and gas.

In another embodiment, a capacitance probe for determining in-situ water content of a conductive fluid, has at least three electrodes, wherein a first and a second electrode comprising: a thin, pliable and conductive wire or winding; and a thin layer or coating of an insulating material, wherein the insulating material covers the conductive wire. The first electrode is configured as a sensing or measurement electrode, and the second electrode is configured as a guard electrode. The guard electrode is configured to steer an electric field in a preferred measurement direction. The guard electrode is configured to receive a guard signal. The guard electrode is driven with at the same voltage potential as the measurement electrode. The capacitance probe can be located within a body of a logging tool. The tool body is configured as a third/grounding electrode. The measurement electrode and the grounding electrode are configured to form a capacitance sensor that generates a signal related to the dielectric permittivity of the conductive fluid, wherein the conductive fluid flows over and between the measurement electrode and the grounding electrode.

DETAILED DESCRIPTION

Figure 1:
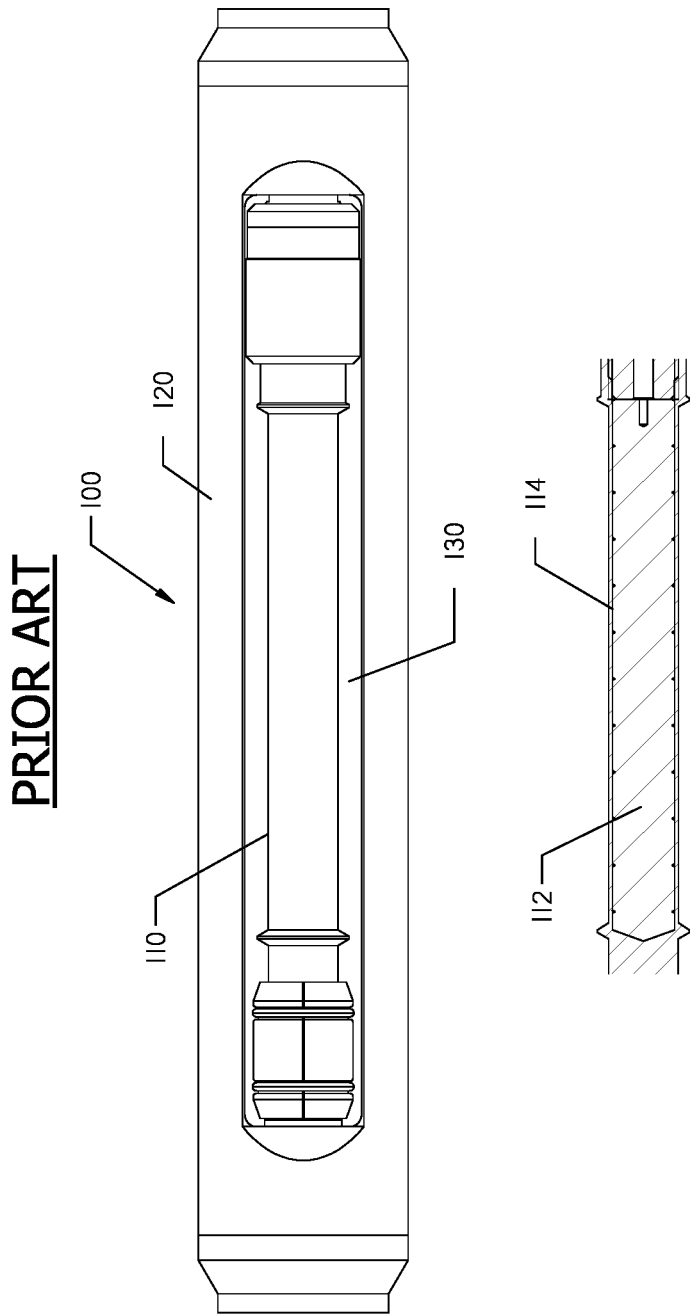
FIG. 1 illustrates a prior art capacitance probe.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Wherever the phrases "for example," "such as," "including" and the like are used herein, the phrase "and without limitation" is understood to follow unless explicitly stated otherwise. Therefore, "for example thermoplastic polymers" means "for example and without limitation thermoplastic polymers" including other plastics and insulators, suitable for use in the oil and gas wells.

The terms "involving", "comprising" and "including" (and similarly "involves", "comprises" and "includes") are used interchangeably and mean the same thing. Specifically, each of the terms is defined consistent with the common United States patent law definition of "comprising" and is therefore interpreted to be an open term meaning "at least the following" and also interpreted not to exclude additional features, limitations, aspects, etc.

The term "about" is meant to account for variations due to experimental error and/or measurement error or limitations.

The terms "electrode" and "insulated winding" are used interchangeably herein. As used herein, the term "winding" refers to a thin, flexible, electrically conductive wire.

The one or more embodiments of the present invention relate to a wet gas capacitance probe or sensor. The probe can be configured for determining water cut or in-situ water content of a medium, such as, a surrounding fluid or fluid flowing through a tool. The fluid can include a multiphase mixture of water, oil and gas and/or solids in a subsurface environment. In one embodiment, the fluid is a wellbore fluid.

Conventional downhole capacitance probes are typically based on a single central larger diameter cylindrical electrode insulated with PEEK, ceramic or other non-conductive material. Conventional downhole capacitance probes are susceptible to continuous thin films of conductive fluid, such as, water, due to the large diameter central electrode which causes the probe to wet or read spuriously higher capacitance values. Also, due to the large diameter of the central electrode, the insulation requirement is typically five to ten times more, which further reduces the sensitivity of these conventional probe to the dielectric properties of the surrounding fluids.

The one or more embodiments of the present invention disclose the use of at least two electrodes comprising thin, flexible insulated wires/windings. This increases the effective length and area of the capacitance probe of the present invention, while maintaining a relative short profile. It also facilitates the spacing and proximity of a first electrode relative to a secondary electrode which can enhance the fluid dynamics of the probe. The use of two or more electrodes as an insulated wire minimizes and/or eliminates the influence of the tool body as a conductor, which further minimizes issues related to wetting and thereby, improving capacitance measurement. Additionally, using one or more of the electrodes as a guard focuses the measurement on the produced fluids. The guard electrode can improve the sensitivity of measurement, providing a better measurement of the produced fluids.

Furthermore, the use of windings in the probe has several benefits. It can increase the measurement dynamic range and measurement accuracy by enabling the use of thin insulation material (less than 50 mils or 0.05 inches as opposed to 50-150 mils in a conventional capacitance probe at pressure). Furthermore, the measurement dynamic range and measurement accuracy is increased by increasing the effective length and area of the probe. As described earlier, it also reduces the chances of and the effect of wetting. The windings ensure that capacitance measurement has equal weighting for all fluids that flow over the surface of the probe which ensures better representation of the fluids flowing in the well. The use of flexible and insulated windings as electrodes further optimizes the shape and structure of the capacitance probe to improve the measurement.

Figure 2A:
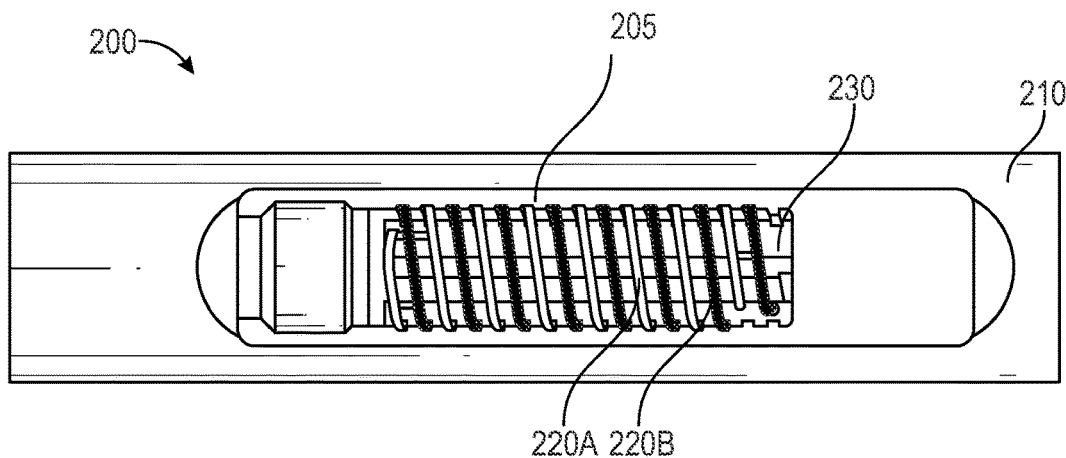
FIGS. 2A and 2C-2D illustrate a capacitance probe, according to an embodiment.
Figure 2B:
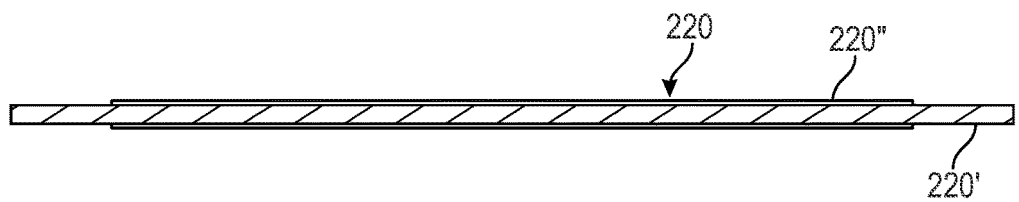
FIG. 2B illustrates an exemplary insulated winding, according to an embodiment.
Figure 2C:
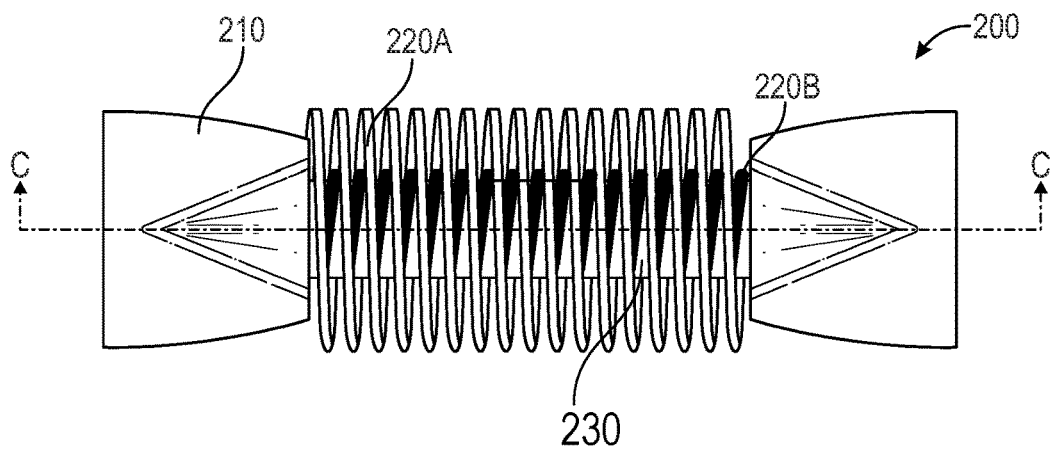
Figure 2D:
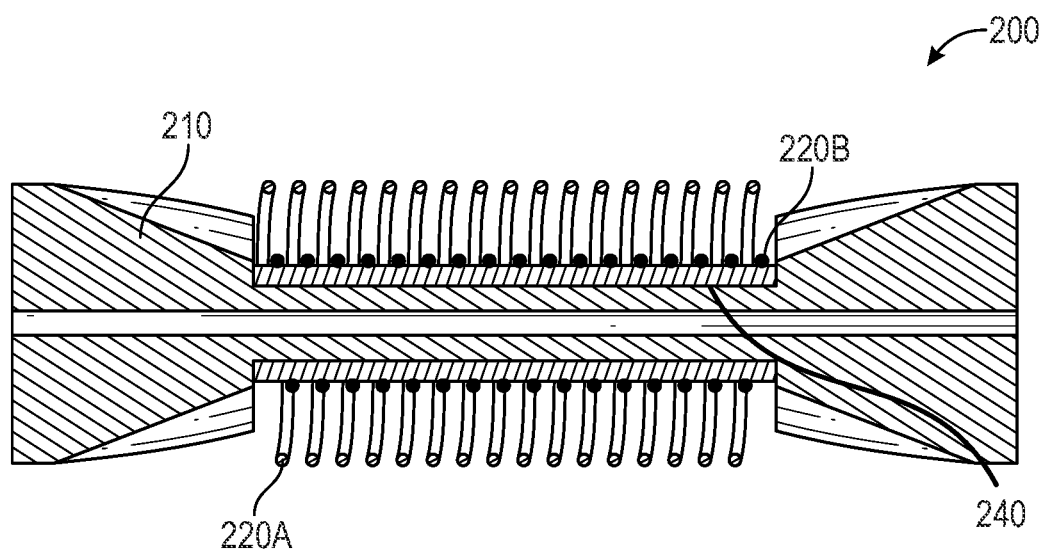

FIGS. 2A and 2C-2D illustrate an embodiment 200 of the probe 205. As shown, the probe 205 is positioned within a production logging tool body 210. The probe 205 comprises a pair of electrodes, 220A, 220B (together "electrodes 220").

As shown in FIG. 2B, each electrode 220 includes a winding/wire 220' and an outer insulation material 220". The winding 220' is made of a thin, pliable, conductive wire/coil. The length of the insulated windings can be configured to optimize the capacitance measurements. In an exemplary embodiment, the shape of the winding resembles a circular coil. In another exemplary embodiment, the shape of the winding is similar to a sinusoidal or square wave projected onto a cylinder.

In another embodiment, the probe 205 can include a housing (not shown) wherein the housing has any arbitrary shape. For instance, the housing can be elliptical or circular in shape. In another example, the housing can be rectangular in shape. The housing can be configured to function as a ground electrode.

The use of thin windings in turn facilitates use of a thin insulation material 220". This enhances or maximizes the response of the probe 205. In one embodiment, the winding 220' comprises an 18 AWG-24 AWG electrical wire/cable with 0.12 inches thick of FEP insulation. The insulation material 220" can include a thermoplastic or a thermosetting polymer. In a specific embodiment, the insulation material is PEEK. However, the insulation material 220' can include any other type of polymer, ceramic or non-conductive material. In certain embodiments, the insulation material 220" can be applied as a high temperature coating, such as, varnish or polyamide, or glass (enamel) for high temperature operation. The radius of the winding 220' is specifically configured to facilitate a reduction in the thickness of the insulation material 220". Advantageously, the winding 220' is only covered with a thin or ultra-thin layer of insulation material 220". This facilitates a substantially accurate measurement of the dielectric permittivity of any intervening fluid. In one embodiment, the insulation material has a thickness of about 0.005 inches—0.015 inches. In one specific embodiment, the insulation material is 0.010 inches in thickness. This increases the dynamic range of the capacitance probe by 200% or greater from traditional probes, thereby providing increased sensitivity to small changes in water content.

Now referring back to FIG. 2A, the electrodes 220A, 220B are wound on an insulated mount 240. In one embodiment, the insulated winding of the first electrode 220A can be configured to be parallel with the insulated winding of the second electrode 220B. This ensures that the probe 205 has a substantially large effective surface area that is sensitive to a conductive fluid (not shown) that can flow between the two electrodes 220. At least one of the two electrodes, for instance, the second electrode 220B, can be isolated electrically from the fluid.

The probe 205 measures the dielectric capacity of the fluid that flows over the two electrodes 220. The electrodes 220A, 220B are sensitive to the fluid that flows over and between the surface of the electrodes. In this embodiment, the tool body 210 does not influence the measurement. The effect of any wetting does not have a disproportionate influence on the measurement as all measurements can be made in a similar proximity to the measured fluid. The range of this measurement is limited to near surface of the electrodes 220.

Each electrode 220A, 220B approximates a separate equal potential field. In one exemplary embodiment, the two electrodes 220A, 220B can be driven with an AC signal 180 degrees out of phase, and the capacitance is measured between the two electrodes. The location of the electrodes 220A, 220B can be arranged to minimize the impact of fluid fallback along the tool body 210, thereby minimizing the effect of wetting caused by the conductive fluid creating an equal potential field on the surface of the electrodes 220. Neither of the electrodes 220 is required to be at the same potential as the tool body 210.

As shown in FIGS. 2C-2D, since the two electrodes 220A, 220B are isolated from each other, the effect of any surface wetting on either electrode can be minimized. In one or more embodiments, two equipotential fields—an inner and an outer field—can be created between the electrodes 220A, 220B and the dielectric permittivity of the fluid that is circulating between the electrodes is measured. Advantageously, due to the configuration of the electrodes, each electrode can be driven with an AC signal that is 180 degrees apart to allow for an improved measurement of the water cut.

As shown in FIG. 2C, electrode 220B can be positioned abutting the mount 230. FIG. 2D shows a cross-section view of FIG. 2C. The second electrode 220A can be positioned at a predetermined distance from electrode 220B. As described earlier with reference to FIG. 2B, the electrodes 220A, 220B comprise a winding with a thin layer or coating of an insulation material. Since the outer electrodes used to create an equal potential field is also a winding, and fluid can easily flow between the electrodes, the spacing between the electrodes 220A, 220B can be decreased. And, since the spacing is decreased, the capacitance is increased. Conductive fluid flows in the annulus between the electrodes 220. In accordance with an embodiment, the dielectric permittivity of the fluid flowing in the annulus between these two electrodes 220A, 220B can be measured.

The electrodes 220 can be located inside an insulating sleeve 240. The sleeve 240 can also function as a ground electrode. The sleeve 240 can be configured to have any desired shape. In one exemplary embodiment, the sleeve 240 can be circular or elliptical in shape. In another embodiment, the sleeve 240 can be rectangular or square in shape. As shown in FIG. 2F, the sleeve 240 can have one or more elongated slots or openings 245 to allow the ingress and egress of the conducting fluid.

In one or more embodiments, two single pin high pressure feedthroughs or one dual pin high pressure feedthrough (not shown) can be used to connect the electrodes placed within a wellbore to the electronics located inside the tool body 210. These types of feedthroughs and electronics are known in the art.

Figure 2E:
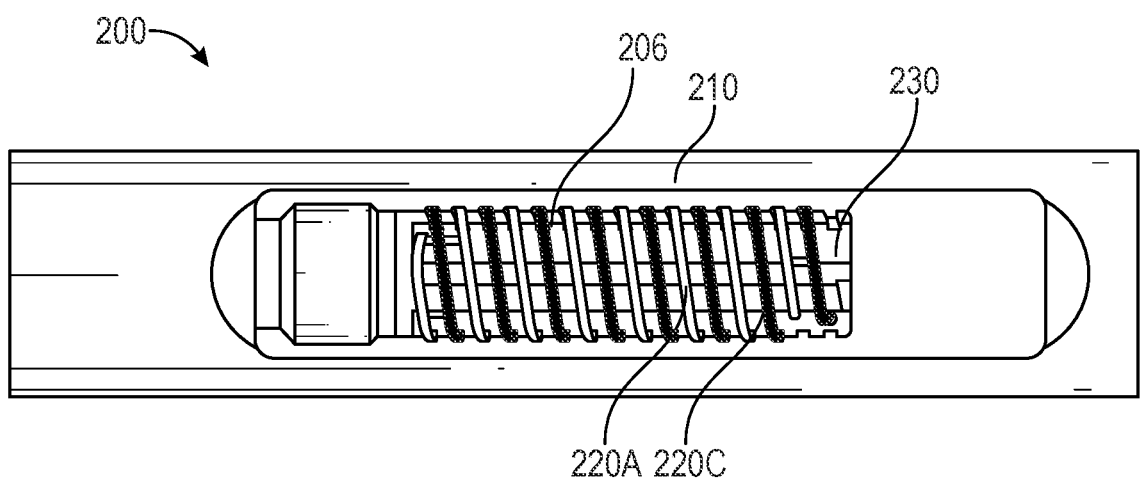
FIG. 2E illustrate a capacitance probe with a guard electrode, according to another embodiment.
Figure 2F:
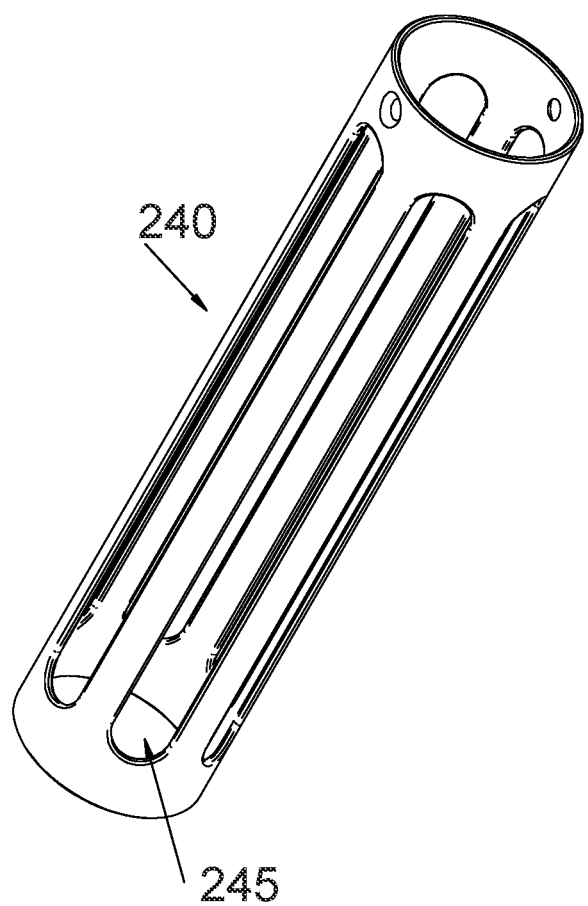
FIG. 2F illustrates an exemplary insulated sleeve, according to an embodiment.

The probe 206 disclosed in FIG. 2E is substantially similar to the probe 205 disclosed in FIG. 2A, with the exception that the second electrode is driven as a guard electrode 220C. Guarding of sensor electrodes is an important principle in the design of capacitance sensors. The objective of capacitance sensors is to measure the capacitance between a sensing element or electrode and a target electrode. The use of the guard electrode 220C prevents the sensing or measurement electrode 220A from seeing the difference in voltage potential of other elements in its signal path. This can be done by actively driving a guard signal with the same potential as the measurement electrode 220A. In the case of the measurement electrode 220A, the guard signal focuses the electric field such that the voltage potential of any unwanted elements does not interfere with the principal electric field of the measurement electrode. The driven guard electrode 220C eliminates or nullifies the influence of unwanted interference of voltage potential at either end of the probe or outer edges of the measurement area from impacting the capacitance measurement. This include wetting from liquids that may be falling along the tool body.

In FIG. 2E, electrode 220A is used to measure the capacitance between itself and the tool body 210. The guard electrode 220C is driven with at the same voltage potential as the measurement electrode 220A. This can focus the sensitivity of the capacitance measurement in a desired direction to measure the dielectric properties of the fluid with minimal effects from wetting. The guard electrode 220C creates an equipotential electric field such that the measurement electrode does not see the effects or loads of other voltage potentials that interfere with the measurement direction. This can provide a better measurement of the fluids between the measurement electrode and the tool body while still minimizing the impact of wetting. Since the measurement electrode 220A can be sensitive to the conductive fluids that flow between the measurement electrode and target electrode, the probe 206 has reduced sensitivity to the conductive fluids that may wet the probe 206. The use of the guard signal will further minimize the impact of disturbances to the electric field near the surface and edges of the probe by maintaining an electric field that is at the same potential as the measurement electrode 220A.

In one or more embodiments, the probe can include more than two windings to configure an array of measurements.

In one or more embodiments, a plurality of probes 205, 206 can be positioned in the tool body. The number and arrangement of the probes may depend on the desired measurement/fluid to be measured.

In another embodiment, a method for determining the water content of a multiphase wellbore fluid mixture involves providing a probe having at least one pair of insulated windings. One of the insulated windings is used as a primary electrode while the second insulated winding is configured either as a secondary electrode or a guard electrode. The apparatus can be positioned within a logging tool. When the secondary electrode is configured as a guard electrode, the body of the tool is configured as a grounding electrode. The primary electrode and the grounding electrode, or the primary electrode and the second electrode, are configured to form a capacitance probe to determine the dielectric permittivity of the fluid flowing over and around the electrodes. Using any conventional power supply, alternating current can be provided to the electrodes. In general, the more water there in the fluid mixture, the higher its capacitance. The capacitance probe can be sampled multiple times a second using a downhole electronic circuit. The capacitance probe can be configured to provide signals proportional to the capacitance of the fluid mixture. The signals can be either transmitted to the surface by a wireline telemetry system or it can be stored downhole in non-volatile memory for later retrieval and processing. The method may further involve pre-determining the dielectric constants of the various components of the fluid. The signals can be processed in a dedicated and conventional processor, and based on the predetermined dielectric constants, the water cut of the multiphase fluid mixture can be determined.

Each insulated winding of the present invention creates an electric field that is substantially different from that created by a solid axial rod or primary electrode of a conventional capacitance probe. The shape and spacing between the insulated windings further create a very different electric field with distinct advantage over prior art capacitance probes. The windings create a substantially equipotential electrical field or virtual surface to form the capacitance electrodes. This is different from the field created by a single electrode or array of electrodes whose surface creates the equipotential field. The insulated windings allow the shape and position of the electric field to be closer to the secondary electrode (or the ground electrode) without reducing the liquid volume that would be taken up by an equivalent solid large, insulated electrode of a conventional capacitance probe. This characteristic provides an increase in dynamic range of the measurement that is four to five times that of conventional capacitance probe due to the lower capacitance in air, and significant higher capacitance in water.

In one or more embodiments, the surface of the insulated windings can further be provided with a non-wetting surface to enhance the accuracy of measurements.

The one or more embodiments of the probes disclosed herein are configured to avoid the problems associated with the design of conventional probes by ensuring that the fluid flow seen by the probe is homogenous and representative of the mixture of fluids (oil, water, gas). The probes facilitate an increase in both the accuracy and sensitivity of measurement to small changes in the water cut. The probes can be used in any application where it is necessary to determine water cut or the amount of water in a mixture or fluid stream. The probes—when glass is used as the insulating material for the windings—can be used in extremely high temperatures, such as, at 350° C.

The probes can be used by upstream oil and gas companies. In one embodiment, the apparatus can be used in wet gas wells to improve the accuracy of water content measurements. The water content information can be used by operating companies, including independent, medium and large multi-national companies, and national oil companies.

A number of embodiments have been described. Nevertheless, it will be understood that various modifications may be made without departing from the spirit and scope of the invention. Accordingly, other embodiments are included as part of the invention and may be encompassed by the attached claims. Furthermore, the foregoing description of various embodiments does not necessarily imply exclusion. For example, "some" embodiments or "other" embodiments may include all or part of "some", "other" and "further" embodiments within the scope of this invention.

We claim:

1. A capacitance probe for determining in-situ water content of a fluid, comprising:
    at least two electrodes, each electrode comprising:
        a thin, pliable and conductive wire or winding; and
        a thin layer or coating of an insulating material, wherein the insulating material covers the conductive wire,
    a first electrode is configured as a primary electrode, and a second electrode is configured as a secondary electrode, and
    wherein the primary electrode and the secondary electrode are separated from each other by a predetermined distance,
    wherein the capacitance probe is positioned in a body of a production logging tool,
    wherein the primary electrode and the secondary electrode are configured to form a capacitance sensor that generates a signal related to a dielectric permittivity of the fluid,
    wherein the fluid flows over and between the primary electrode and the secondary electrode, and
    wherein at least one of the electrode windings creates an equipotential electrical field to form a capacitance electrode.

2. The capacitance probe according to claim 1, wherein the primary electrode is arranged parallel to the secondary electrode such that the capacitance probe has a substantially large effective surface area that is sensitive to the fluid.

3. The capacitance probe according to claim 2, wherein the secondary electrode is electrically isolated from the fluid.

4. The capacitance probe according to claim 1, wherein the insulating material is a thermosetting polymer.

5. The capacitance probe according to claim 1, further comprising a sleeve for the at least two electrodes.

6. The capacitance probe according to claim 1, wherein the fluid comprises a multiphase mixture of water, oil and gas.

7. A capacitance probe for determining in-situ water content of a fluid, comprising:
    at least three electrodes, wherein a first and a second electrode comprising:
        a thin, pliable and conductive wire or winding; and
        a thin layer or coating of an insulating material, wherein the insulating material covers the conductive wire,
    the first electrode is configured as a sensing or measurement electrode, and the second electrode is configured as a guard electrode,
    wherein the capacitance probe is located within a body of a logging tool,
    wherein the tool body is configured as a third electrode,
    wherein the first/measurement electrode and the third electrode are configured to form a capacitance sensor that generates a signal related to the dielectric permittivity of the fluid,
    wherein the fluid flows over and between the first electrode and the third electrode, and
    wherein the winding of the second/guard electrode steers an electric field in a desired direction to measure dielectric properties of the fluid with minimal effects from wetting.

8. The capacitance probe according to claim 7, wherein the second/guard electrode is configured to receive a guard signal.

9. The capacitance probe according to claim 8, wherein the guard signal is driven with a same voltage potential as the measurement electrode.

10. The capacitance probe according to claim 7, wherein the fluid comprises a multiphase mixture of water, oil and gas.

* * * * *